United States Patent
Ohyama et al.

(10) Patent No.: US 11,452,465 B2
(45) Date of Patent: Sep. 27, 2022

(54) ACTION DETERMINATION APPARATUS AND ACTION DETERMINATION METHOD

(71) Applicant: SHARP KABUSHIKI KAISHA, Sakai (JP)

(72) Inventors: Shigeo Ohyama, Sakai (JP); Hajime Kubota, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 917 days.

(21) Appl. No.: 16/091,906

(22) PCT Filed: Apr. 3, 2017

(86) PCT No.: PCT/JP2017/013961
§ 371 (c)(1),
(2) Date: Oct. 5, 2018

(87) PCT Pub. No.: WO2017/175720
PCT Pub. Date: Oct. 12, 2017

(65) Prior Publication Data
US 2019/0110717 A1    Apr. 18, 2019

(30) Foreign Application Priority Data
Apr. 8, 2016    (JP) .............................. JP2016-078397

(51) Int. Cl.
*A61B 5/11* (2006.01)
*A61B 5/00* (2006.01)

(52) U.S. Cl.
CPC .......... *A61B 5/1123* (2013.01); *A61B 5/0002* (2013.01); *A61B 5/1118* (2013.01); *A61B 5/1121* (2013.01); *A61B 5/4866* (2013.01); *A61B 2562/0219* (2013.01)

(58) Field of Classification Search
CPC ... A61B 5/1123; A61B 5/1118; A61B 5/1121; A61B 5/112; A61B 5/1114
USPC ....................................................... 600/595
See application file for complete search history.

(56) References Cited

U.S. PATENT DOCUMENTS

| | | | |
|---|---|---|---|
| 2010/0191697 A1 | 7/2010 | Fukumoto et al. | |
| 2012/0291544 A1 | 11/2012 | Kawabe | |
| 2013/0274587 A1 | 10/2013 | Coza et al. | |
| 2014/0032476 A1 | 1/2014 | Fukumoto et al. | |
| 2016/0030807 A1* | 2/2016 | Matsumoto .............. | A61B 5/11 600/595 |

(Continued)

FOREIGN PATENT DOCUMENTS

| | | | |
|---|---|---|---|
| JP | 2010-198595 A | 9/2010 | |
| JP | 2011-200390 A | 10/2011 | |

(Continued)

*Primary Examiner* — Daniel L Cerioni
*Assistant Examiner* — Deirdre M Willgohs
(74) *Attorney, Agent, or Firm* — ScienBiziP, P.C.

(57) ABSTRACT

Regarding acceleration on each of three axes Gx, Gy, and Gz calculated by a microcomputer, acceleration on one of the three axes is acceleration in a vertical direction perpendicular to the ground, and acceleration on each of the other two axes is acceleration in a direction parallel to the ground, the other two axes being perpendicular to each other. A type of action of the human body in a predetermined period is determined by comparing a predetermined threshold value with the acceleration in the vertical direction in the predetermined period.

3 Claims, 5 Drawing Sheets

(56) References Cited

U.S. PATENT DOCUMENTS

| | | | |
|---|---|---|---|
| 2016/0074667 A1* | 3/2016 | Sullivan | A61B 5/361 607/6 |
| 2016/0262685 A1* | 9/2016 | Wagner | A61B 5/1123 |
| 2016/0275403 A1 | 9/2016 | Fukumoto et al. | |
| 2017/0056720 A1* | 3/2017 | Coza | A61B 5/1112 |

FOREIGN PATENT DOCUMENTS

| JP | 2012-178164 A | 9/2012 |
|---|---|---|
| JP | 2013-190371 A | 9/2013 |
| JP | 2013-220356 A | 10/2013 |

* cited by examiner

ACTION DETERMINATION APPARATUS AND ACTION DETERMINATION METHOD

TECHNICAL FIELD

The present invention relates to an action determination apparatus and an action determination method.

BACKGROUND ART

Currently, there are many activity meters that not only count the number of steps during walking but also determine an action state such as walking or running so as to determine respective calories burned and calculate an accurate total calorie expenditure.

For example, when a user runs at a relatively slow speed, it may sometimes be difficult for an activity meter of the related art to distinguish between running and walking in terms of specifying the action type.

As a technique for solving the above problem, an activity meter described in Patent Document 1 may be exemplified. The activity meter described in Patent Document 1 measures, in accordance with detection output of an acceleration sensor, the number of steps each time a predetermined fixed period elapses. Further, for each "section representing signal change caused by body motion for one step", the amplitude of a difference between the maximum value and the minimum value of the detection output of the acceleration sensor is detected. Then, depending on whether or not the amplitude is equal to or greater than the threshold value v, the activity meter specifies whether the body motion for one step to be processed is caused by walking or running. A first threshold value TH and a second threshold value TL are set for the signal detected by the acceleration sensor. A change in the signal detected in a period of time from when the signal detected by the acceleration sensor is greater than the first threshold value TH to when the signal detected is equal to or less than the second threshold value TL is assumed as a change in signal caused by the body motion for one step. The "section representing the change in signal caused by the body motion for one step" is defined as a period of time from when the signal detected is greater than the first threshold value TH to when the signal detected is equal to or less than the second threshold value TL.

As described above, according to the activity meter described in Patent Document 1, it is possible to prevent the action type from being inaccurately specified.

CITATION LIST

Patent Literature

PTL 1: Japanese Unexamined Patent Application Publication No. 2011-200390 (Publication Date: Oct. 13, 2011)

SUMMARY OF INVENTION

Technical Problem

In the activity meter described in Patent Document 1, the difference between the maximum value and the minimum value of the acceleration sensor is determined in accordance with the threshold value v. Since this difference is relatively large between walking and running, walking can be distinguished even from slow running.

However, when walking with intense vertical oscillation due to notable bending of the knees, the difference between the maximum value and the minimum value of the acceleration is large. Then, if the difference is greater than the threshold value v, the walking is erroneously recognized as running.

The present invention has been made in view of the above-mentioned problems, and the object of the present invention is to realize an action determination apparatus capable of performing action determination more accurately.

Solution to Problem

In order to solve the above-mentioned problems, an action determination apparatus according to an embodiment of the present invention includes: a three-axis acceleration sensor that measures acceleration on each of three axes Sx, Sy, and Sz; and a microcomputer that calculates acceleration on each of three axes Gx, Gy, and Gz of a human body from the acceleration on each of the three axes Sx, Sy, and Sz. Regarding the acceleration on each of the three axes Gx, Gy, and Gz calculated by the microcomputer, acceleration on one of the three axes is acceleration in a vertical direction perpendicular to the ground, and acceleration on each of the other two axes is acceleration in a direction parallel to the ground, the other two axes being perpendicular to each other. The microcomputer determines a type of action of the human body in a predetermined period by comparing a predetermined threshold value with the acceleration in the vertical direction in the predetermined period.

Advantageous Effects of Invention

According to an embodiment of the present invention, even in the case of walking with intense vertical oscillation due to notable bending of the knees, it is possible to determine the action more accurately without erroneously recognizing the walking as running.

BRIEF DESCRIPTION OF DRAWINGS

FIG. 1(a) illustrates a state in a case of walking, FIG. 1(b) illustrates a state in a case of running, and FIG. 1(c) illustrates a state in a case of jumping.

FIG. 2(a) illustrates a state at the time of foot off, and FIG. 2(b) illustrates a state at the time of foot strike.

FIG. 4(a) illustrates a state at the time of ascent, and FIG. 4(b) illustrates a state at the time of descent.

FIG. 6 is a schematic diagram in which FIG. 6(a) illustrates a resultant acceleration of acceleration on each of the three axes in a case of walking or running and FIG. 6(b) illustrates a resultant acceleration in a case of jumping.

FIG. 7 is a waveform diagram in which FIG. 7(a) illustrates a resultant acceleration in a case of walking or running and FIG. 7(b) illustrates a resultant acceleration in a case of jumping.

DESCRIPTION OF EMBODIMENTS

Figure 1:
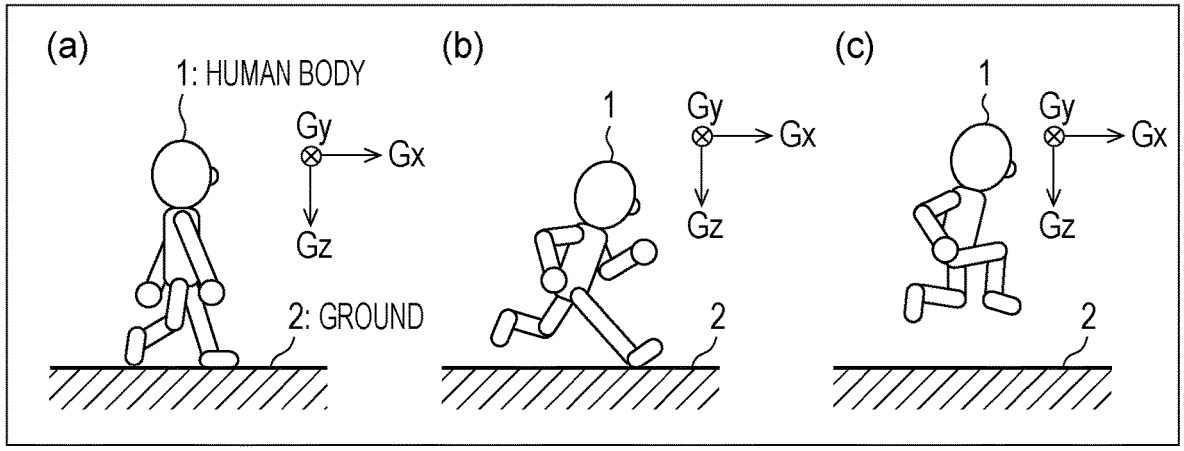
FIG. 1 is a schematic diagram illustrating an example of a type of action of a human body to be determined by an action determination apparatus according to Embodiment 1 of the present invention.

Embodiments of the present invention will be described below with reference to FIGS. 1 to 9.

Embodiment 1

FIGS. 1(a) to 1(c) are schematic diagrams illustrating examples of types of action of a human body 1 to be determined by an action determination apparatus according to Embodiment 1 of the present invention. FIG. 1(a) illustrates a state in a case of walking, FIG. 1(b) illustrates a state in a case of running, and FIG. 1(c) illustrates a state in a case of jumping. In this case, the term, which is simply described as the jumping, means jumping on the spot, that is, jumping only in the vertical direction.

FIGS. 2(a) and 2(b) are schematic diagrams illustrating the forces applied to the human body 1 in the state of the human body 1 illustrated in FIG. 1(a) in a case of walking. FIG. 2(a) illustrates a state at the time of foot off, and FIG. 2(b) illustrates a state at the time of foot strike.

There are three types of action of the human body 1 determined by the action determination apparatus: walking; running; and jumping. The action determination apparatus includes: a three-axis acceleration sensor that measures acceleration on each of three axes Sx, Sy, and Sz; and a microcomputer that calculates acceleration on each of three axes Gx, Gy, and Gz of a human body from the acceleration on each of the three axes Sx, Sy, and Sz. Regarding the acceleration on each of the three axes Gx, Gy, and Gz calculated by the microcomputer, acceleration on one of the three axes is acceleration in a vertical direction perpendicular to the ground, and acceleration on each of the other two axes is acceleration in a direction parallel to the ground, the other two axes being perpendicular to each other. The microcomputer compares a predetermined threshold value with the acceleration in the vertical direction in the predetermined period (the comparison step) and thereby determines a type of action of the human body in a predetermined period (the first determination step).

Here, it is assumed that one of the three axes regarding the acceleration on each of the three axes Gx, Gy, and Gz corresponds completely with the acceleration in the vertical direction perpendicular to the ground. Further, it is assumed that the acceleration on each of the other two axes is parallel to the ground, the other two axes being perpendicular to each other. Specifically, it is assumed that the acceleration Gz corresponds with the acceleration in the vertical direction perpendicular to the ground and that the acceleration Gx and the acceleration Gy each correspond with the acceleration in a direction parallel to the ground and in directions perpendicular to each other. It is assumed that the acceleration Gz is in the direction toward the ground 2, that the acceleration Gx is in the direction of movement of the human body 1, and that the acceleration Gy is in the left direction as viewed in the direction of movement of the human body 1. Further, the three axes of acceleration on each of the three axes Sx, Sy, and Sz of the three-axis acceleration sensor do not correspond with the three axes of acceleration on each of the three axes Gx, Gy, and Gz of the human body 1, respectively. That is, the axes of Sx and Gx do not correspond with each other, the axes of Sy and Gy do not correspond with each other, and the axes of Sz and Gz do not correspond with each other.

Further, the predetermined threshold value is a value sufficiently smaller than an acceleration of 1 G at rest. Since the actual three-axis acceleration sensor has a measurement error, it may not be assumed that the acceleration in the vertical direction is exactly equal to or less than zero. Therefore, it is practical to use a value, which is sufficiently smaller than the acceleration of 1 G at rest, for example 0.1 G, as a criterion for determination. However, in the following description, it is assumed that there is no measurement error in the three-axis acceleration sensor. The predetermined period is a predetermined fixed period of time. In the predetermined period, the microcomputer detects that the acceleration in the vertical direction is equal to or less than zero. Thereby, the action determination apparatus determines the type of action of the human body 1 in the predetermined period. Further, for example, the action determination apparatus is attached to the lumbar part of the human body 1, thereby determining the type of action of the human body 1. The place, to which the action determination apparatus is attached, may be the trunk, the neck, or the head of the human body 1.

(Case of Walking)

As illustrated in FIG. 1(a), in a case of walking, the human body 1 is consistently in contact with the ground 2. As a result, as illustrated in FIGS. 2(a) and 2(b), in a case of walking, a normal force 3 is applied to the human body 1.

As illustrated in FIG. 2(a), at the time of foot off, the normal force 3, the ground reaction force 4a, and the gravitational force 5 are applied to the human body 1. Since the normal force 3 is applied to the human body 1 from the ground 2, the direction of the normal force 3 is opposite to the direction toward the ground 2. Since one foot of the human body 1 is necessarily in contact with the ground in a case of walking, a normal force 3 exists.

Here, it is assumed that the ground reaction force 4a is a force that the ground 2 exerts on the human body 1 such that the human body 1 ascends. Further, the ground reaction force 4a occurs when the human body 1 lifts a foot from the ground. At the time of foot off, the ground reaction force 4a from the ground 2 is exerted on the human body 1 in a direction opposite to the direction toward the ground 2. As a result, the direction of the ground reaction force 4a is opposite to the direction toward the ground 2.

Since the gravitational force 5 is an attractive force applied to the human body 1 by the earth, the direction of the gravitational force 5 is in the direction toward the ground 2 from the human body 1. According to the law of action and reaction, the gravitational force 5 is equal to the sum of the magnitude of the normal force 3 and the magnitude of the ground reaction force 4a.

Further, the three-axis acceleration sensor is used to determine the acceleration of the human body 1. The value of the acceleration in the vertical direction is obtained by dividing the resultant force of the ground reaction force 4a and the gravitational force 5 by the mass of the human body 1. When the acceleration is calculated using a three-axis acceleration sensor, the acceleration of the human body 1 is separated into the acceleration in the vertical direction perpendicular to the ground 2 and the acceleration in the horizontal direction with respect to the ground 2. Here, the direction toward the ground 2 is set to be positive in terms of the acceleration in the vertical direction.

At the time of foot off, the direction of the ground reaction force 4a is opposite to the direction toward the ground 2. Therefore, the direction of the ground reaction force 4a and the direction of the gravitational force 5 are opposite to each other. Therefore, at the time of foot off, the acceleration of the human body 1 in the vertical direction is less than 1 G. G (m/s²) is a unit of the gravitational acceleration. Accordingly, the state in which the acceleration in the vertical direction at the time of foot off is 1 G means a state where the ground reaction force 4a is zero, that is, the ground reaction force 4a is not applied to the human body 1. If the direction of the ground reaction force 4a and the direction of the gravitational force 5 are opposite to each other, the sum of the ground reaction force 4a and the gravitational force 5 is less than that when the ground reaction force 4a is zero. That is, if the direction of the ground reaction force 4a and the direction of the gravitational force 5 are opposite to each other, the acceleration of the human body 1 in the vertical direction is less than 1 G.

The action determination apparatus may be attached in a state where one measurement axis of the three-axis acceleration sensor is oriented in the vertical direction. The action determination apparatus may calculate the direction of the gravitational force 5 from the acceleration on each of the three axes Gx, Gy, and Gz in accordance with the direction of gravitational acceleration at rest. However, in practice, it is difficult to perfectly match the direction of the gravitational force 5 with one of the measurement axes of the three-axis acceleration sensor. Therefore, when the action determination apparatus is attached to the human body 1, the axes of the acceleration on each of the three axes Gx, Gy, and Gz of the human body 1 deviate from the axes of the acceleration on each of the three axes Sx, Sy, and Sz of the three-axis acceleration sensor. Therefore, calculation is performed to correct the acceleration on each of the three axes Sx, Sy, and Sz of the three-axis acceleration sensor to acceleration on each of the three axes Gx, Gy, and Gz of the human body 1.

First, the human body 1 is made stationary, and the directions of the axes of acceleration on each of the three axes Gx, Gy, and Gz of the human body 1 are determined in accordance with the measurement result of the gravitational acceleration obtained when the human body 1 remains stationary. Next, by attaching the action determination apparatus to the human body 1, the directions of the axes of acceleration on each of the three axes Sx, Sy, and Sz of the three-axis acceleration sensor are determined.

Next, angles φ, θ, and ψ are calculated from the directions of the axes of the acceleration on each of the three axes Gx, Gy, and Gz of the human body 1 and the directions of the axes of the acceleration on each of the three axes Sx, Sy, and Sz of the three-axis acceleration sensor. The angle θ is an angle between the axis of the acceleration Gz and the axis of the acceleration Sz. Further, in a case where the angle θ is not 0 degrees or 180 degrees, the GxGy plane and the SxSy plane intersect with each other at one straight line. The straight line is denoted by N. The angle φ is an angle between the axis of the acceleration Sx and the straight line N. The angle ψ is an angle between the axis of the acceleration Gx and the straight line N.

Next, the three-axis acceleration sensor measures the acceleration on each of the three axes Sx, Sy, and Sz (the measurement step). Further, the microcomputer calculates acceleration on each of the three axes Gx, Gy, and Gz of the human body 1 from the acceleration on each of the three axes Sx, Sy, and Sz of the three-axis acceleration sensor in accordance with the following Expression (1) (Euler's formula) (the calculation step).

[Expression 1]

$$\begin{pmatrix} Gx \\ Gy \\ Gz \end{pmatrix} = \begin{pmatrix} \cos\psi & \sin\psi & 0 \\ -\sin\psi & \cos\psi & 0 \\ 0 & 0 & 1 \end{pmatrix} \begin{pmatrix} 1 & 0 & 0 \\ 0 & \cos\theta & \sin\theta \\ 0 & -\sin\theta & \cos\theta \end{pmatrix} \begin{pmatrix} \cos\phi & \sin\phi & 0 \\ -\sin\phi & \cos\phi & 0 \\ 0 & 0 & 1 \end{pmatrix} \begin{pmatrix} Sx \\ Sy \\ Sz \end{pmatrix} \quad (1)$$

$$= \begin{pmatrix} \cos\psi\cos\phi - \sin\psi\cos\theta\sin\phi & \cos\psi\sin\phi + \sin\psi\cos\theta\cos\phi & \sin\psi\sin\theta \\ -\sin\psi\cos\phi - \cos\psi\cos\theta\sin\phi & -\sin\psi\sin\phi + \cos\psi\cos\theta\cos\phi & \cos\psi\sin\theta \\ \sin\theta\sin\phi & -\sin\theta\cos\phi & \cos\theta \end{pmatrix} \begin{pmatrix} Sx \\ Sy \\ Sz \end{pmatrix}$$

As illustrated in FIG. 2(b), at the time of foot strike, a normal force 3, a pressing force 4b, and a gravitational force 5 are applied to the human body 1. Here, the pressing force 4b is a force that the human body 1 exerts on the ground 2. Further, the pressing force 4b occurs when a foot of the human body 1 strikes the ground.

Difference between the time of foot off and the time of foot strike is in that the direction of the pressing force 4b applied to the human body 1 at the time of foot strike is opposite to the direction of the ground reaction force 4a. At the time of foot off, the human body 1 tries to move itself in a direction opposite to the direction toward the ground 2. In contrast, at the time of foot strike, the human body 1 applies a force in the direction toward the ground 2. As a result, at the time of foot strike, the direction of the pressing force 4b becomes equal to the direction toward the ground 2.

According to the law of action and reaction, the gravitational force 5 is equal to a value obtained by subtracting the magnitude of the pressing force 4b from the magnitude of the normal force 3. The acceleration in the vertical direction, which can be measured by the three-axis acceleration sensor, is a value obtained by dividing the resultant force of the pressing force 4b and the gravitational force 5 by the mass of the human body 1.

Further, at the time of foot strike, the direction of the pressing force 4b is the direction toward the ground 2. Therefore, the direction of the pressing force 4b and the direction of the gravitational force 5 are the same direction. In other words, at the time of foot strike, the acceleration of the human body 1 in the vertical direction is greater than 1 G. Accordingly, the state in which the acceleration in the vertical direction at the time of foot strike is 1 G means a state in which the pressing force 4b is zero, that is, the pressing force 4b is not applied to the human body 1. If the direction of the pressing force 4b and the direction of the gravitational force 5 are the same, the sum of the forces of the pressing force 4b and the gravitational force 5 is greater than that when the pressing force 4b is zero. That is, if the direction of the pressing force 4b and the direction of the gravitational force 5 are the same, the acceleration of the human body 1 in the vertical direction is greater than 1 G.

Figure 3:
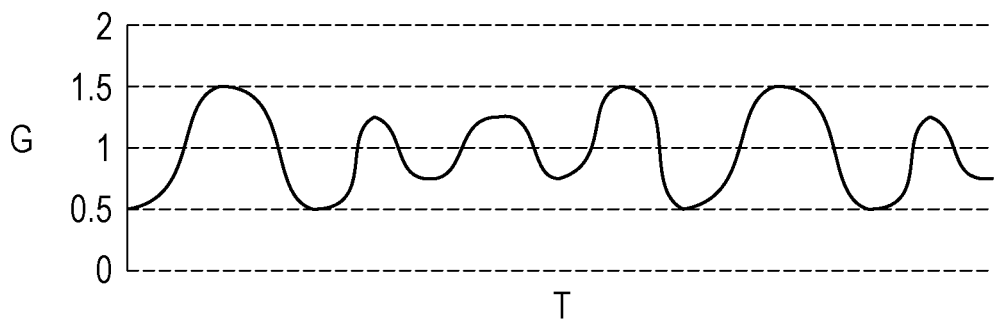
FIG. 3 is a waveform diagram illustrating an example of acceleration in a vertical direction perpendicular to the ground in a case of walking.

FIG. 3 is a waveform diagram illustrating an example of the acceleration in the vertical direction perpendicular to the ground 2 in a case of walking. In FIG. 3, the vertical axis represents the acceleration of the human body 1 in the vertical direction. The horizontal axis represents the time T.

As illustrated in FIG. 3, in a case of walking, as the time T elapses, the following cycle is repeated: the acceleration in the vertical direction increases above 1 G and decreases below 1 G in a state where the gravitational acceleration of 1 G is at the center. Further, as long as the human body 1 is in contact with the ground 2, the normal force 3 is a value greater than zero. Therefore, the acceleration of the human body 1 in the vertical direction in the measurement of the three-axis acceleration sensor is not zero.

Figure 2:
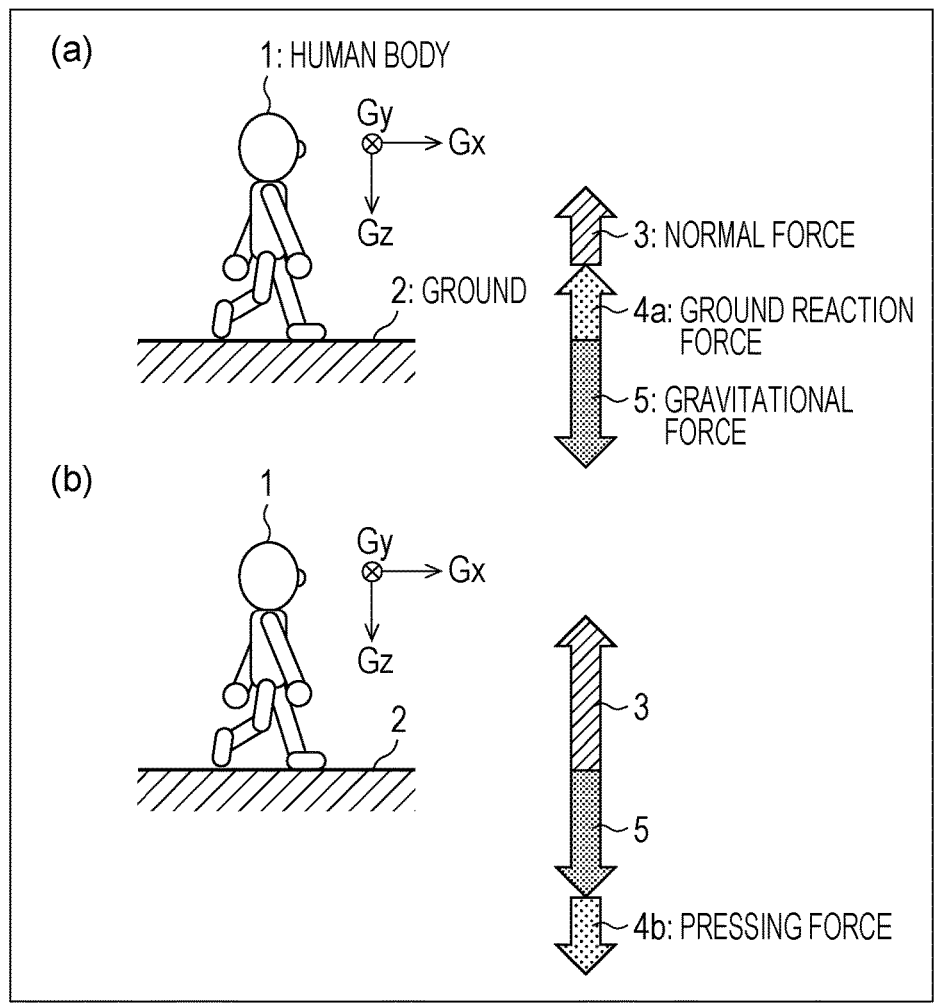
FIG. 2 is a schematic diagram illustrating forces applied to the human body in the state of the human body in a case of walking illustrated in FIG. 1(a).

Accordingly, in a case of walking, as can be seen from FIGS. 2 and 3, the following cycle is repeated: the acceleration of the human body 1 in the vertical direction decreases below 1 G at the time of foot off, and the acceleration of the human body 1 in the vertical direction increases above 1 G at the time of foot strike in a state where the acceleration of 1 G is at the center. The magnitude of the amplitude of the acceleration of the human body 1 in the vertical direction changes in accordance with the manner of walking or individual differences, but in a case of walking, the acceleration of the human body 1 in the vertical direction is consistently greater than zero. Accordingly, the action determination apparatus is able to determine that the action of the human body 1 is walking by detecting that the acceleration in the vertical direction is consistently greater than zero (the predetermined threshold value) in the predetermined period (the third determination step). The predetermined threshold value is a value sufficiently smaller than the acceleration of 1 G at rest. Since the actual three-axis acceleration sensor has a measurement error, it may not be assumed that the acceleration in the vertical direction is consistently greater than zero exactly. Therefore, it is practical to use a value, which is sufficiently smaller than the acceleration of 1 G at rest, for example 0.1 G, as a criterion for determination. In the above description, it is assumed that there is no measurement error in the three-axis acceleration sensor.

(Case of Running)

Figure 4:
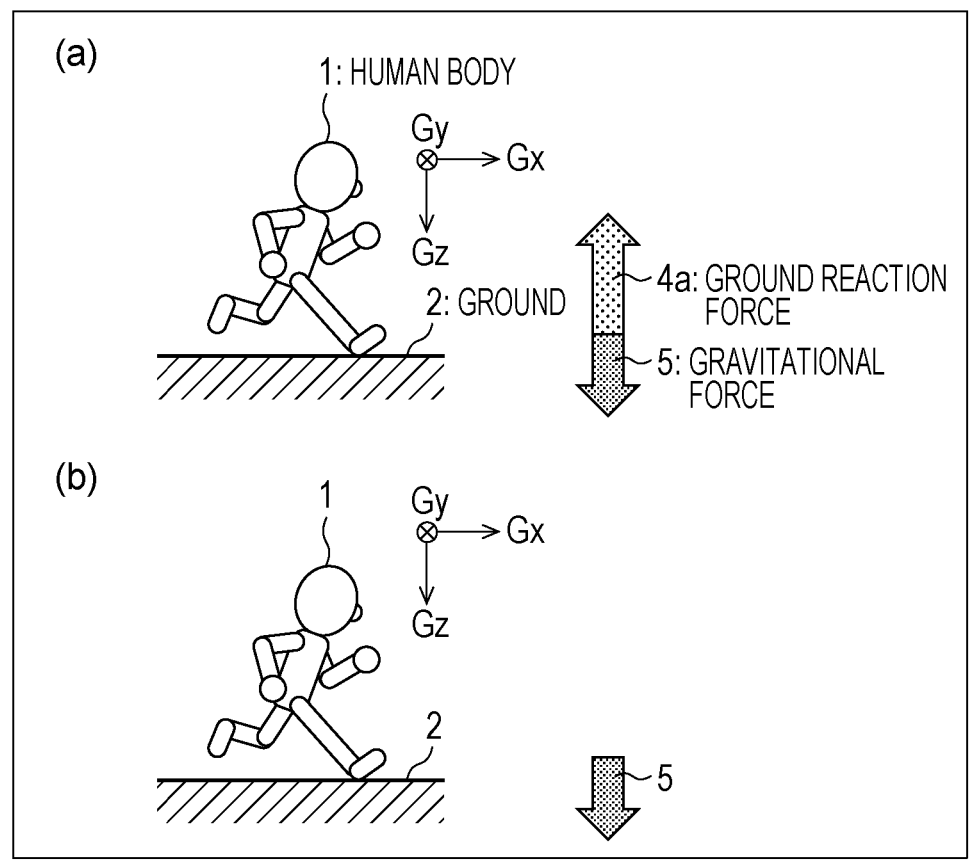
FIG. 4 is a schematic diagram illustrating forces applied to the human body in the state of the human body in a case of running illustrated in FIG. 1(b).

FIGS. 4(*a*) and 4(*b*) are schematic diagrams illustrating the forces applied to the human body 1 in the state of the human body 1 in FIG. 1(*b*) in a case of running. FIG. 4(*a*) illustrates a state at the time of ascent in a case of running, and FIG. 4(*b*) illustrates a state at the time of descent in a case of running. FIGS. 4(*a*) and 4(*b*) each illustrate a state in which the human body 1 is away from the ground 2. In a case of running, when the human body 1 is in contact with the ground 2, the law of action and reaction is established as in walking. However, when both feet of the human body 1 are away from the ground 2, the normal force 3 is lost and the inertial force is at work. The inertial force is represented by the following Expression (2).

$$F = mg - F_1 = ma \quad (2)$$

Here, F is the inertial force, mg is the gravitational force, $F_1$ is the ground reaction force, m is the mass, and a is the acceleration in the vertical direction.

This acceleration a is the acceleration of the human body 1 in the vertical direction which can be measured by the three-axis acceleration sensor. Regarding the direction of the inertial force, assuming that the direction toward the ground 2 is positive, when the human body 1 ascends away from the ground 2, the value of the inertial force is less than zero. Here, it is assumed that there is no measurement error in the three-axis acceleration sensor. When the human body 1 reaches the highest reach point, the inertial force is zero, and at the time of descent, the acceleration of the human body 1 in the vertical direction is 1 G. Specifically, at the time of ascent, the ground reaction force 4*a* is greater than the gravitational force 5. Thus, the value of the inertial force is less than zero. Further, when the human body 1 reaches the highest reach point, the ground reaction force 4*a* and the gravitational force 5 are balanced. Thus, the inertial force is zero. At the time of descent, while the human body 1 is away from the ground 2, neither the ground reaction force 4*a* nor the pressing force 4*b* is applied to the human body 1. Thus, the acceleration of the human body 1 in the vertical direction is 1 G.

In a case of running, the human body 1 fluctuates between being in contact with the ground 2 and being away from the ground 2. Further, while the human body 1 is away from the ground 2, the acceleration in the vertical direction is equal to or less than zero. Thereby, regarding the force applied to the human body 1, in a case of running, the following cycle is repeated: the acceleration in the vertical direction increases above zero and decreases below zero. The magnitude of the amplitude changes in accordance with the manner of walking or individual differences. However, in a case of running, there is a time point when the acceleration in the vertical direction is equal to or less than zero.

As illustrated in FIG. 4(*a*), at the time of ascent, the ground reaction force 4*a* and the gravitational force 5 are applied to the human body 1. Since the human body 1 is away from the ground 2, the normal force 3 is not applied to the human body 1. Further, immediately before the human body 1 is away from the ground 2, the ground 2 exerts the ground reaction force 4*a* upward on the human body 1. Therefore, at the time of ascent, the ground reaction force 4*a* is applied upward to the human body 1. At this time, the direction of the ground reaction force 4*a* is opposite to the direction toward the ground 2. Therefore, the direction of the ground reaction force 4*a* and the direction of the gravitational force 5 are opposite to each other. Consequently, at the time of ascent, the acceleration of the human body 1 in the vertical direction is less than 1 G.

As illustrated in FIG. 4(*b*), only the gravitational force 5 is applied to the human body 1 at the time of descent. As in FIG. 4(*a*), since the human body 1 is away from the ground 2, the normal force 3 is not applied to the human body 1. Further, at the time of descent in a case of running, while the human body 1 is away from the ground 2, the pressing force 4*b*, which is a force that the human body 1 exerts on the ground 2, is not applied to the human body 1. At this time, since only the gravitational force 5 is applied to the human body 1 in the direction toward the ground 2, the acceleration of the human body 1 in the vertical direction is 1 G. When the human body 1 descends and its foot strikes the ground, the pressing force 4*b* is applied in the direction toward the ground 2. Therefore, the acceleration in the vertical direction is greater than 1 G.

Figure 5:
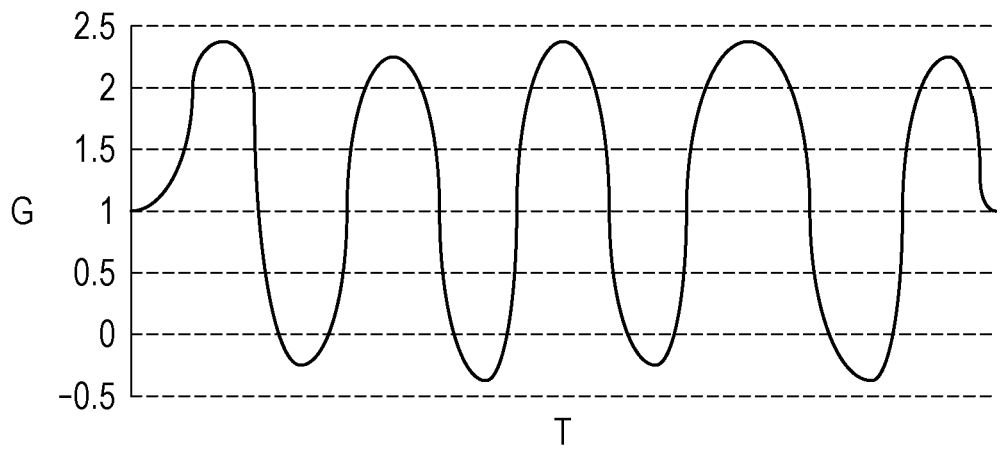
FIG. 5 is a waveform diagram illustrating an example of acceleration in a vertical direction perpendicular to the ground in a case of running.

FIG. 5 is a waveform diagram illustrating an example of the acceleration in the vertical direction perpendicular to the ground 2 in a case of running. In FIG. 5, the vertical axis represents the acceleration of the human body 1 in the vertical direction. The horizontal axis represents the time T.

As illustrated in FIG. 5, in a case of running, as the time T elapses, the following cycle is repeated: the acceleration in the vertical direction increases above 1 G and decreases below 1 G in a state where the acceleration of 1 G is at the center as in walking. A case of running is different from a case of walking in that there is a time point at which the acceleration is equal to or less than zero in terms of the acceleration in the vertical direction. Also in a case of jumping in FIG. 1(*c*), there is a time point at which the acceleration in the vertical direction is equal to or less than zero. Accordingly, the action determination apparatus determines that the action of the human body 1 is walking by detecting that the acceleration in the vertical direction is consistently greater than zero (the predetermined threshold value) in the predetermined period. In addition, the action determination apparatus determines that the action of the human body 1 is running or jumping by detecting that the acceleration in the vertical direction is equal to or less than zero (the predetermined threshold value) in a predetermined period (the second determination step). The predetermined threshold value is a value sufficiently smaller than the acceleration of 1 G at rest. Since the actual three-axis acceleration sensor has a measurement error, it may not be assumed that there is a time point at which the acceleration in the vertical direction is exactly equal to or less than zero. Therefore, it is practical to use a value, which is sufficiently smaller than the acceleration of 1 G at rest, for example 0.1 G, as a criterion for determination. In the above description, it is assumed that there is no measurement error in the three-axis acceleration sensor. Thereby, the action determination apparatus is able to distinguish between walking and running or jumping by detecting that the acceleration in the vertical direction is consistently greater than zero in the predetermined period. As can be seen from FIGS. 4 and 5, in a state where the acceleration of 1 G is at the center, the acceleration in the vertical direction decreases below 1 G at the time of foot off, and the acceleration in the vertical direction decreases below zero when the human body 1 is away from the ground 2, that is, at the time of ascent. Further, when the human body 1 reaches the highest reach point away from the ground 2, the acceleration in the vertical direction is zero. Thereafter, the acceleration in the vertical direction is 1 G at the time of descent, and the acceleration in the vertical direction is greater than 1 G at the time of foot strike.

That is, in a case of running, when the human body 1 is away from the ground 2, the acceleration in the vertical direction is equal to or less than zero. Also in a case of jumping, when the human body 1 moves away from the ground 2, the acceleration in the vertical direction is equal to or less than zero. Thereby, even in a case of walking with intense vertical oscillation due to notable bending of the knees, the human body 1 is not away from the ground 2. Thus, the action determination apparatus does not erroneously recognize walking of the human body 1 as running, and is able to perform action determination more accurately.

(Action Determination Based on Resultant Acceleration Gm)

Figure 6:
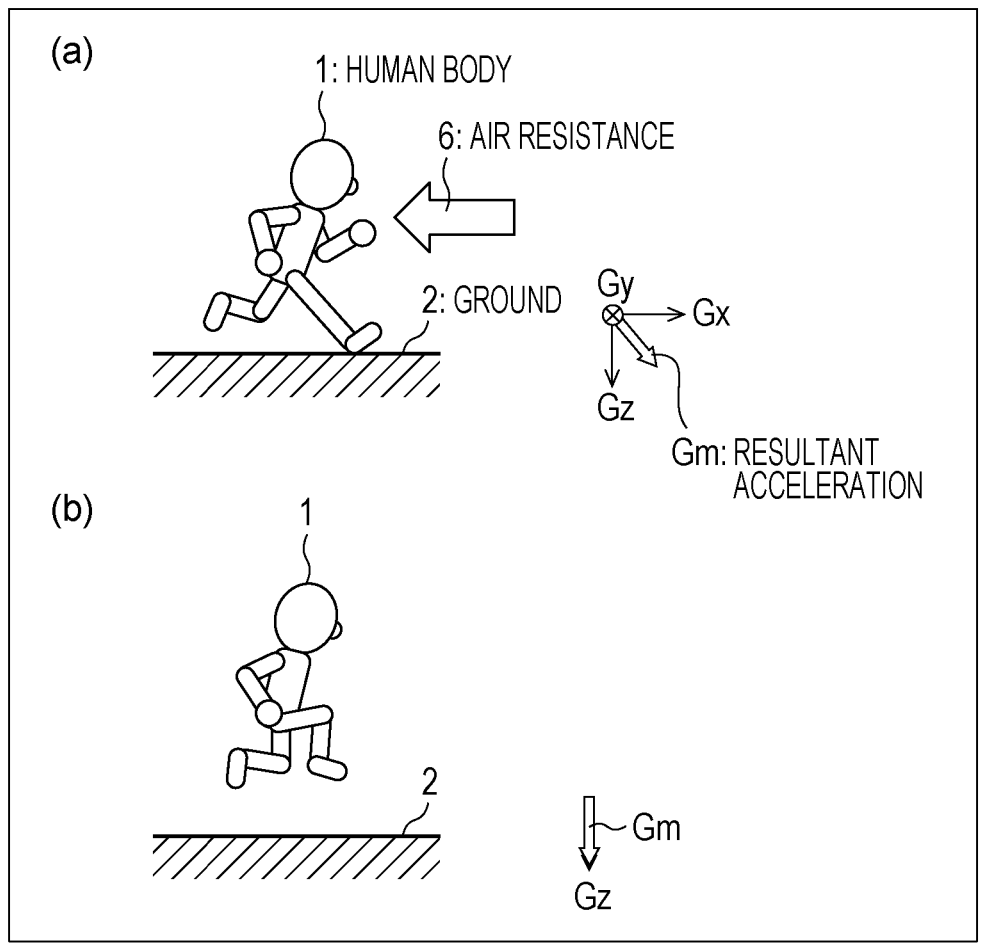

FIGS. 6(*a*) and 6(*b*) are each a schematic diagram illustrating a resultant acceleration Gm of acceleration on each of the three axes in cases of walking, running, and jumping. FIG. 6(*a*) illustrates the resultant acceleration Gm in a case of walking or running. FIG. 6(*b*) illustrates the resultant acceleration Gm in a case of jumping in FIG. 1(*c*). The resultant acceleration Gm is obtained by the following Expression (3).

$$Gm = (Gx^2 + Gy^2 + Gz^2)^{1/2} \quad (3)$$

The microcomputer calculates the resultant acceleration Gm of the acceleration on each of the three axes Gx, Gy, and Gz in accordance with the above Expression (3). Thereby, the action determination apparatus detects that the resultant acceleration Gm is zero. As a result, in the determination of the type of action of the human body 1, the action determination apparatus is able to easily determine the type of action of the human body 1 by using the acceleration in the vertical direction and the resultant acceleration Gm.

When the human body 1 reaches the highest reach point away from the ground 2 in a case of running, the acceleration in the vertical direction is zero. However, as illustrated in FIG. 6(*a*), in a case of running, a force of air resistance 6 acts in a direction opposite to the direction of movement. Accordingly, when the force of the air resistance 6 is exerted on the human body 1, the acceleration of the human body 1 in the direction of movement decreases. That is, in a case of running, the human body 1 has acceleration in the horizontal direction with respect to the ground 2. Thereby, in a case of running, the resultant acceleration Gm is not zero and is consistently greater than zero. Further, in a case of running, the human body 1 may move even in the lateral direction with respect to the direction of movement. Therefore, the resultant acceleration Gm is not zero and is consistently greater than zero.

On the other hand, as illustrated in FIG. 6(*b*), in a case of jumping, since the force of the air resistance 6 is not exerted in the horizontal direction, the acceleration of the human body 1 is only the acceleration in the vertical direction. Thus, at the highest reach point, the acceleration in the vertical direction is zero. As a result, the resultant acceleration Gm is also zero. Thereby, in the predetermined period, the action determination apparatus detects that the acceleration in the vertical direction is equal to or less than zero (the predetermined threshold value) and the resultant acceleration Gm is zero (equal to or less than the predetermined threshold value). At this time, the action determination apparatus determines that the action is jumping (the sixth determination step). The predetermined threshold value is a value sufficiently smaller than the acceleration of 1 G at rest. Since the actual three-axis acceleration sensor has a measurement error, it may not be assumed that the resultant acceleration Gm is exactly equal to zero. Therefore, it is practical to use a value, which is sufficiently smaller than the acceleration of 1 G at rest, for example 0.1 G, as a criterion for determination. In the above description, it is assumed that there is no measurement error in the three-axis acceleration sensor. As described above, in the predetermined period, the action determination apparatus compares the predetermined threshold value with the resultant acceleration Gm of the acceleration on each of the three axes Gx, Gy, and Gz, thereby determining the type of action of the human body 1 (the fourth determination step). Accordingly, the action determination apparatus is able to distinguish between walking or running and jumping by detecting that the resultant acceleration Gm is zero (equal to or less than the predetermined threshold value).

On the other hand, in a case of jumping during running, that is, jumping while running, the human body 1 jumps while advancing in the direction of movement. Therefore, the force of the air resistance 6 is exerted on the human body in the direction opposite to the direction of movement. Accordingly, the resultant acceleration Gm is not zero (equal to or less than the predetermined threshold value). Thus, in a case of jumping while running, the action determination apparatus determines that the action of the human body 1 is running. Therefore, in the predetermined period, the action determination apparatus detects that the acceleration in the vertical direction is equal to or less than the predetermined threshold value and that the resultant acceleration Gm of the acceleration on each of the three axes Gx, Gy, and Gz is consistently greater than zero (the predetermined threshold value). At this time, the action determination apparatus determines that the action of the human body 1 is running which includes jumping while running (the fifth determination step).

Figure 7:
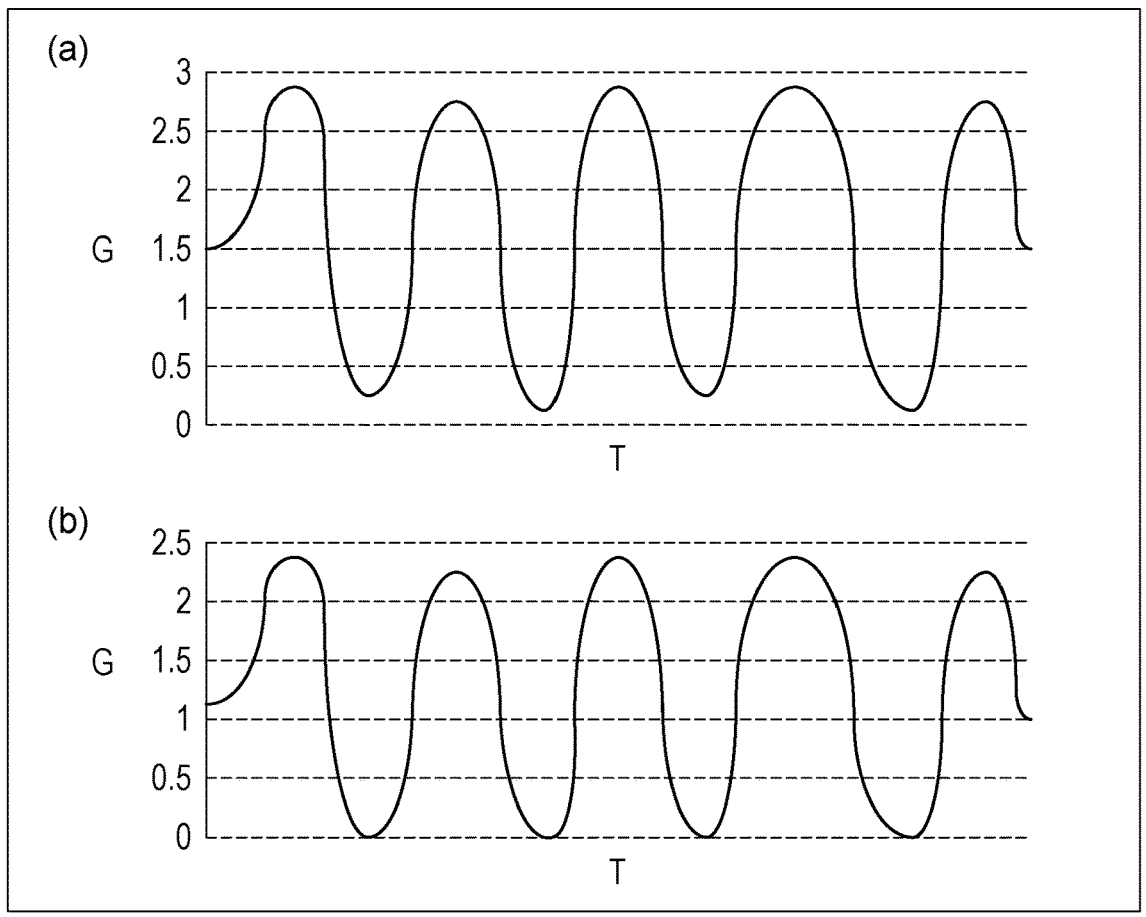

FIGS. 7(*a*) and 7(*b*) are each a waveform diagram illustrating a resultant acceleration Gm in cases of walking, running, and jumping. FIG. 7(*a*) illustrates the waveform of the resultant acceleration Gm in a case of walking or running. FIG. 7(b) illustrates the waveform of the resultant acceleration Gm in a case of jumping. In FIG. 7, the vertical axis represents the resultant acceleration Gm of the human body 1. The horizontal axis represents the time T.

As illustrated in FIGS. 7(a) and 7(b), as time T elapses, the following cycle is repeated: the resultant acceleration Gm increases and decreases in a manner similar to the acceleration in the vertical direction.

As illustrated in FIG. 7(a), the resultant acceleration Gm in a case of walking or running is consistently greater than zero.

As illustrated in FIG. 7(b), there is a time point at which the resultant acceleration Gm in a case of jumping is zero.

Accordingly, compared with the resultant acceleration Gm in a case of walking or running, there is a time point at which the resultant acceleration Gm is zero in a case of jumping. In other words, the action determination apparatus is able to determine that the action is jumping by detecting the time point at which the resultant acceleration Gm is zero.

Table 1 below summarizes the criteria for determination in cases of walking, running, and jumping. By using combinations of the acceleration in the vertical direction and the resultant acceleration Gm for determination, the action determination apparatus is able to distinguish between the states of walking, running, and jumping. In addition, here, it is assumed that there is no measurement error in the three-axis acceleration sensor.

In a case of walking, the acceleration in the vertical direction is consistently greater than zero, and the resultant acceleration Gm is also consistently greater than zero. In a case of running, there is a time point at which the acceleration in the vertical direction is equal to or less than zero. Thus, the resultant acceleration Gm is consistently greater than zero. In a case of jumping, there is a time point at which the acceleration in the vertical direction is equal to or less than zero. Thus, there is a time point at which the resultant acceleration Gm is zero. Accordingly, the action determination apparatus detects that the acceleration in the vertical direction and the resultant acceleration Gm are greater than zero in the predetermined period, thereby determining that the action is walking. In addition, the action determination apparatus detects that the acceleration in the vertical direction is equal to or less than zero and the resultant acceleration Gm is consistently greater than zero in the predetermined period, thereby determining that the action is running which includes jumping while running. The action determination apparatus detects that the acceleration in the vertical direction is equal to or less than zero and that the resultant acceleration Gm is zero, thereby determining that the action is jumping.

Consequently, the action determination apparatus is able to distinguish between the respective states of walking, running and jumping in terms of the acceleration in the vertical direction and the resultant acceleration Gm. In other words, the action determination apparatus is able to determine which of the states of walking, running, and jumping the action of the human body 1 is in.

TABLE 1

| State | Walking | Running | Jumping |
| --- | --- | --- | --- |
| Acceleration in Vertical Direction | Consistently greater than zero | Equal to or less than zero at a certain time | Equal to or less than zero at a certain time |

TABLE 1-continued

| State | Walking | Running | Jumping |
| --- | --- | --- | --- |
| Resultant Acceleration | Consistently greater than zero | Consistently greater than zero | zero at a certain time |

Embodiment 2

Another embodiment of the present invention will be described as follows with reference to FIG. 8.

Figure 8:
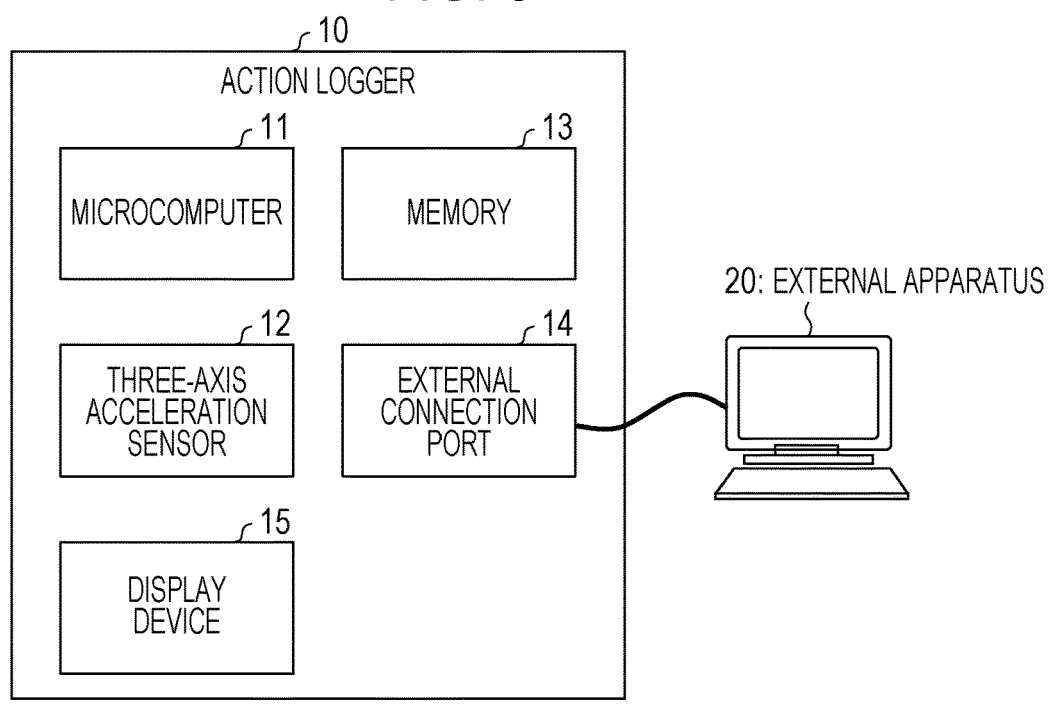
FIG. 8 is a schematic diagram of an example of an action determination apparatus according to Embodiment 2 of the present invention.

FIG. 8 is a schematic diagram of an example of an action determination apparatus according to Embodiment 2 of the present invention.

As illustrated in FIG. 8, an action logger 10 (the action determination apparatus) includes a microcomputer 11, a three-axis acceleration sensor 12, a memory 13, an external connection port 14, and a display device 15.

The microcomputer 11 calculates the acceleration on each of the three axes Gx, Gy, and Gz of the human body 1 from the acceleration on each of the three axes Sx, Sy, and Sz measured by the three-axis acceleration sensor 12, thereby determining the type of action of the human body 1. The three-axis acceleration sensor 12 measures the acceleration on each of the three axes Sx, Sy, and Sz. The memory 13 stores a result of determining the type of action of the human body 1 by the microcomputer 11. The memory 13 may be substituted with a memory built in to the microcomputer 11 or may be substituted with a storage medium such as a removable SD card. The external connection port 14 is for connecting an external apparatus 20 to the action logger 10. As the external connection port 14, a port such as a USB port or a connection port of a serial cable may be used. The display device 15 displays on a screen the result of determining the type of action of the human body 1 by using the microcomputer 11. The display device 15 may be omitted if it is not necessary to display the determination result on a screen.

The external apparatus 20 such as a PC is used to connect to the external connection port 14 of the action logger 10 and to read the result of determining the type of action of the human body 1.

It is assumed that the action logger 10 stores actions of a wearer of the action logger 10 for a certain period (for example, while awake) and thereafter reads the actions. That is, the action logger 10 stores the type of action, which is determined by the microcomputer 11 from the detection result of the three-axis acceleration sensor 12, as data and connects the external connection port 14 to the external apparatus 20, thereby transmitting the data to the external apparatus 20 (the first communication step). Further, the action logger 10 stores the number of times of walking, the number of times of running, and the number of times of jumping and connects the external apparatus 20 to the action logger 10. Thereby, it is possible to calculate the total calories consumed in a measured period. Accordingly, the action logger 10 is able to measure the acceleration of the human body 1 and is able to output data to the outside. The data includes the number of times of walking, the number of times of running, and the number of times of jumping. As described above, the action logger 10 is able to thereafter read the data, which is stored in the memory 13 while the human body 1 is active, to the external apparatus 20. Therefore, the action logger 10 is able to store data of the result of the human body 1 having various activities and thereafter read the data to the external apparatus 20.

Embodiment 3

Another embodiment of the present invention will be described as follows with reference to FIG. 9. For convenience of description, members having the same functions as the members described in the above embodiments are denoted by the same reference numerals, and description thereof will be omitted.

Figure 9:
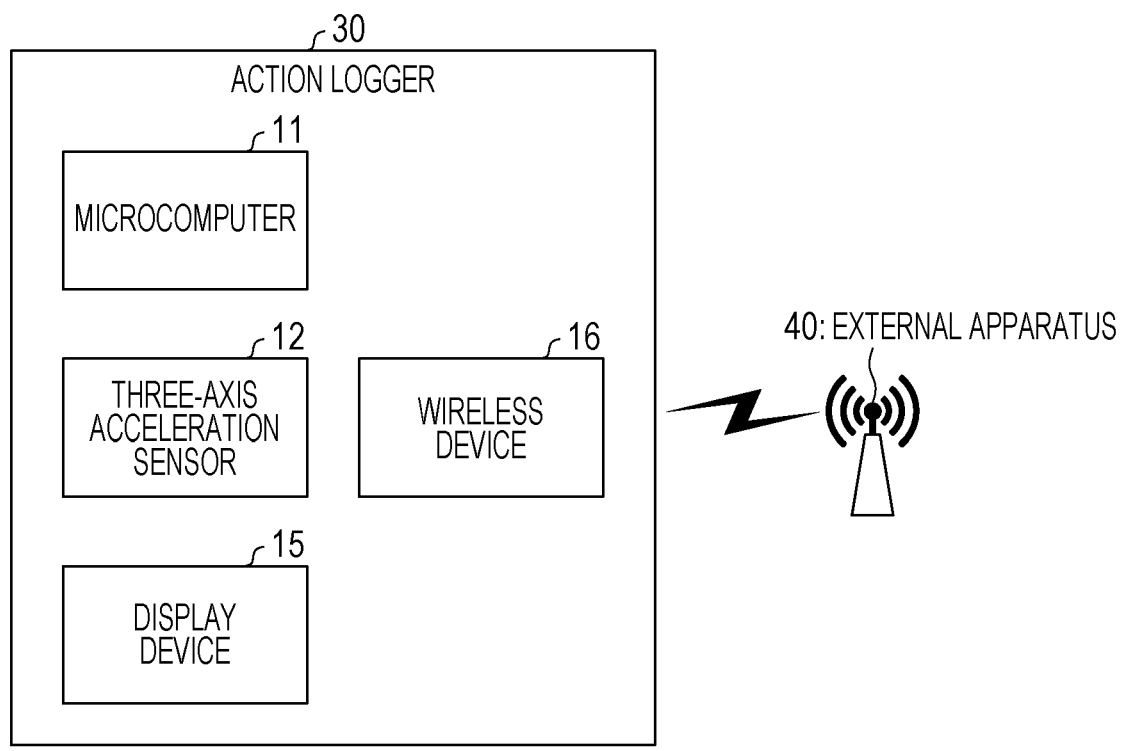
FIG. 9 is a schematic diagram of an example of an action determination apparatus according to Embodiment 3 of the present invention.

FIG. 9 is a schematic diagram of an example of an action determination apparatus according to Embodiment 3 of the present invention.

As illustrated in FIG. 9, the action logger 30 (the action determination apparatus) includes a microcomputer 11, a three-axis acceleration sensor 12, a memory 13, a display device 15, and a wireless device 16.

The memory 13, which stores the result of determining the type of action of the human body 1 by using the microcomputer 11, may be built in to the microcomputer 11. Further, as the memory 13, a removable storage medium such as an SD card may be used. The wireless device 16 communicates with the external apparatus 40 (the second communication step). The wireless device 16 is a device for wirelessly transmitting the data of the result of determining the type of action of the human body 1 to the external apparatus 40. Further, Wi-Fi (registered trademark), Bluetooth (registered trademark), or the like may be used for the wireless device 16, but it is not limited to a specific system. The display device 15 may be omitted if it is not necessary to display the determination result on a screen.

The external apparatus 40 communicates with the action logger 30 and thereby receives data on the result of determining the type of action of the human body 1.

It is assumed that the action logger 30 is used for detecting the current state of the wearer of the action logger 30 in real time. Therefore, the action logger 30 determines the type of action of the human body 1 in real time. Thereby, it is possible to monitor the action of the human body 1.

[Conclusion]

The action determination apparatus according to Embodiment 1 of the present invention includes: a three-axis acceleration sensor that measures acceleration on each of three axes Sx, Sy, and Sz; and a microcomputer that calculates acceleration on each of three axes Gx, Gy, and Gz of a human body from the acceleration on each of the three axes Sx, Sy, and Sz. Regarding the acceleration on each of the three axes Gx, Gy, and Gz calculated by the microcomputer, acceleration on one of the three axes is acceleration in a vertical direction perpendicular to the ground, and acceleration on each of the other two axes is acceleration in a direction parallel to the ground, the other two axes being perpendicular to each other. The microcomputer determines a type of action of the human body in a predetermined period by comparing a predetermined threshold value with the acceleration in the vertical direction in the predetermined period.

According to the above-mentioned configuration, the acceleration of the human body 1 in the vertical direction is compared with the predetermined threshold value. Thus, even in the case of walking with intense vertical oscillation due to notable bending of the knees, the action determination apparatus is able to perform the action determination more accurately without erroneously recognizing the walking as running.

Regarding the action determination apparatus according to Embodiment 2 of the present invention, in the above-mentioned Embodiment 1, the microcomputer detects that the acceleration in the vertical direction is equal to or less than the predetermined threshold value in the predetermined period. Thereby, the microcomputer determines that the action of the human body is running or jumping.

According to the above-mentioned configuration, the action determination apparatus is able to distinguish between walking and running or jumping by detecting that the acceleration in the vertical direction is equal to or less than the predetermined threshold value in the predetermined period.

Regarding the action determination apparatus according to Embodiment 3 of the present invention, in the above-mentioned Embodiment 1, the microcomputer detects that the acceleration in the vertical direction is consistently greater than the predetermined threshold value in the predetermined period. Thereby, the microcomputer determines that the action of the human body is walking.

According to the above-mentioned configuration, the action determination apparatus has the same advantages as those of the above-mentioned Embodiment 2.

Regarding the action determination apparatus according to Embodiment 4 of the present invention, in any one of the above-mentioned Embodiments 1 to 3, the microcomputer compares the predetermined threshold value with the resultant acceleration of the acceleration on each of the three axes Gx, Gy, and Gz in the predetermined period. Thereby, the microcomputer determines the type of action of the human body.

According to the above-mentioned configuration, in the determination of the type of action of the human body 1, the action determination apparatus is able to easily determine the type of action of the human body 1 by using the acceleration in the vertical direction and the resultant acceleration Gm.

Regarding the action determination apparatus according to Embodiment 5 of the present invention, in the above-mentioned Embodiment 4, the microcomputer detects that the acceleration in the vertical direction is equal to or less than the predetermined threshold value and the acceleration in the vertical direction is consistently greater than the predetermined threshold value in the predetermined period. Thereby, the microcomputer determines that the action of the human body is running which includes jumping while running.

According to the above-mentioned configuration, the action determination apparatus is able to determine that the action of the human body 1 is running.

Regarding the action determination apparatus according to Embodiment 6 of the present invention, in the above-mentioned Embodiment 4, the microcomputer detects that the acceleration in the vertical direction is equal to or less than the predetermined threshold value and the resultant acceleration is equal to or less than the predetermined threshold value in the predetermined period. Thereby, the microcomputer determines that the action of the human body is jumping.

According to the above-mentioned configuration, the action determination apparatus is able to determine that the action of the human body 1 is jumping.

In any one of the above-mentioned Embodiments 1 to 6, the action determination apparatus according to Embodiment 7 of the present invention further includes an external connection port and communicates with an external apparatus via the external connection port connected to the external apparatus.

According to the above-mentioned configuration, the action determination apparatus is able to output data to the outside. The data includes the result of determining the types of action of the human body 1 such as the number of times of walking, the number of times of running, and the number of times of jumping. Further, the action determination apparatus is able to thereafter read the data, which is stored in the memory 13 while the human body 1 is active, to the external apparatus 20. Therefore the action determination apparatus is able to store data of the result of the human body 1 having various activities and thereafter read the data to the external apparatus 20.

In any one of the above-mentioned Embodiments 1 to 6, the action determination apparatus according to Embodiment 8 of the present invention includes a wireless device and communicates with the outside via the wireless device.

According to the above-mentioned configuration, the action determination apparatus determines the type of action of the human body 1 in real time. Thereby, it is possible to monitor the action of the human body 1.

An action determination method according to Embodiment 9 of the present invention includes a measurement step, a calculation step, a comparison step, and a first determination step. The measurement step is a step of measuring acceleration on each of three axes Sx, Sy, and Sz by using the three-axis acceleration sensor. The calculation step is a step of calculating acceleration on each of three axes Gx, Gy, and Gz in the human body from the acceleration on each of the three axes Sx, Sy, and Sz by using the microcomputer. The comparison step is a step of comparing the predetermined threshold value with the acceleration in the vertical direction in the predetermined period by using the microcomputer. Regarding the acceleration on each of the three axes Gx, Gy, and Gz calculated by the microcomputer, acceleration on one of the three axes is the acceleration in the vertical direction perpendicular to the ground, and acceleration of each of the other two axes is acceleration in a direction parallel to the ground, and the other two axes being perpendicular to each other. The first determination step is a step of determining the type of action of the human body in the predetermined period.

According to the above-mentioned configuration, the action determination method has the same advantages as those of the above-mentioned Embodiment 1.

Regarding the action determination method according to Embodiment 10 of the present invention, in the above-mentioned Embodiment 9, the first determination step includes a second determination step of determining that the action of the human body is running or jumping when the acceleration in the vertical direction is equal to or less than the predetermined threshold value in the predetermined period.

According to the above-mentioned configuration, the action determination method has the same advantages as those of the above-mentioned Embodiment 2.

Regarding the action determination method according to Embodiment 11 of the present invention, in the above-mentioned Embodiment 9, the first determination step includes a third determination step of determining that the action of the human body is walking when the acceleration in the vertical direction is consistently greater than the predetermined threshold value in the predetermined period.

According to the above-mentioned configuration, the action determination method has the same advantages as those of the above-mentioned Embodiment 3.

Regarding the action determination method according to Embodiment 12 of the present invention, in any one of the above-mentioned Embodiments 9 to 11, the first determination step includes a fourth determination step of determining the type of action of the human body by comparing the predetermined threshold value with a resultant acceleration of acceleration on each of the three axes Gx, Gy, and Gz by using the microcomputer.

According to the above-mentioned configuration, the action determination method has the same advantages as those of the above-mentioned Embodiment 4.

Regarding the action determination method according to Embodiment 13 of the present invention, in the above-mentioned Embodiment 12, the first determination step includes a fifth determination step of determining that the action of the human body is running including jumping while running by detecting that the acceleration in the vertical direction is equal to or less than the predetermined threshold value and that the resultant acceleration is consistently greater than the predetermined threshold value in the predetermined period.

According to the above-mentioned configuration, the action determination method has the same advantages as those of the above-mentioned Embodiment 5.

Regarding the action determination method according to Embodiment 14 of the present invention, in the above-mentioned Embodiment 12, the first determination step includes a sixth determination step of determining that the action of the human body is jumping by detecting that the acceleration in the vertical direction is equal to or less than the predetermined threshold value and that the resultant acceleration is equal to or less than the predetermined threshold value in the predetermined period.

According to the above-mentioned configuration, the action determination method has the same advantages as those of the above-mentioned Embodiment 6.

In any one of the above-mentioned Embodiments 9 to 14, the action determination method according to Embodiment 15 of the present invention further includes a first communication step of communicating with an external apparatus via an external connection port connected to the external apparatus.

According to the above-mentioned configuration, the action determination method has the same advantages as those of the above-mentioned Embodiment 7.

In any one of the above-mentioned Embodiments 9 to 14, the action determination method according to Embodiment 16 of the present invention further includes a second communication step of communicating with the outside via a wireless device.

According to the above-mentioned configuration, the action determination method has the same advantages as those of the above-mentioned Embodiment 8.

REFERENCE SIGNS LIST

1 HUMAN BODY
2 GROUND
3 NORMAL FORCE
4*a* GROUND REACTION FORCE
4*b* PRESSING FORCE
5 GRAVITATIONAL FORCE
6 AIR RESISTANCE 10, 30 ACTION LOGGER (ACTION DETERMINATION APPARATUS)
11 MICROCOMPUTER
12 THREE-AXIS ACCELERATION SENSOR
13 MEMORY
14 EXTERNAL CONNECTION PORT
15 DISPLAY DEVICE
16 WIRELESS DEVICE
20, 40 EXTERNAL APPARATUS
Gm RESULTANT ACCELERATION

The invention claimed is:

1. An action determination apparatus comprising:
a three-axis acceleration sensor configured to measure acceleration on each of three axes Sx, Sy, and Sz; and
a microcomputer configured to calculate acceleration on each of three axes Gx, Gy, and Gz of a human body from the acceleration on each of the three axes Sx, Sy, and Sz,
wherein regarding the acceleration on each of the three axes Gx, Gy, and Gz calculated by the microcomputer, acceleration on one of the three axes is acceleration in a vertical direction perpendicular to the ground, and acceleration on each of the other two axes is acceleration in a direction parallel to the ground, the other two axes being perpendicular to each other,
wherein the microcomputer is configured to determine a type of action of the human body in a predetermined period by comparing zero with the acceleration in the vertical direction in the predetermined period,
wherein the microcomputer is configured to determine the type of action of the human body by comparing zero with a resultant acceleration of the acceleration on each of the three axes Gx, Gy, and Gz in the predetermined period,
wherein the microcomputer is configured to determine that the action of the human body is an action including both running and jumping when detecting that the acceleration in the vertical direction is equal to or less than zero and that the resultant acceleration is consistently greater than zero in the predetermined period, and
wherein the microcomputer is configured to determine that the action of the human body is jumping when detecting that the acceleration in the vertical direction is equal to or less than zero and that the resultant acceleration is equal to or less than zero in the predetermined period.

2. The action determination apparatus according to claim 1, further comprising
an external connection port,
wherein the action determination apparatus is configured to communicate with an external apparatus via the external connection port to the external apparatus.

3. The action determination apparatus according to claim 1, further comprising
a wireless device,
wherein the action determination apparatus is configured to communicate with an external apparatus via the wireless device.

* * * * *